United States Patent
Muller et al.

(10) Patent No.: US 8,716,311 B2
(45) Date of Patent: May 6, 2014

(54) USE OF PIPERIDINE ESTER DERIVATIVE AS SOLVENT IN COSMETIC COMPOSITIONS; COSMETIC COMPOSITIONS COMPRISING IT

(75) Inventors: Benoit Muller, Paris (FR); Herve Richard, Gagny (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/499,363

(22) PCT Filed: Oct. 2, 2009

(86) PCT No.: PCT/EP2009/062817
§ 371 (c)(1),
(2), (4) Date: Jul. 10, 2012

(87) PCT Pub. No.: WO2011/038776
PCT Pub. Date: Apr. 7, 2011

(65) Prior Publication Data
US 2012/0282197 A1     Nov. 8, 2012

(51) Int. Cl.
*A61K 8/49*     (2006.01)
*A61K 8/40*     (2006.01)
*A61K 31/445*   (2006.01)
*A61Q 17/04*    (2006.01)

(52) U.S. Cl.
CPC .......... *A61K 8/4926* (2013.01); *A61K 8/40* (2013.01); *A61K 31/445* (2013.01); *A61Q 17/04* (2013.01)
USPC .......................... 514/315; 424/401

(58) Field of Classification Search
USPC .......................... 424/401; 514/315
See application file for complete search history.

(56) References Cited

FOREIGN PATENT DOCUMENTS

FR     2931066 A1 * 11/2009

OTHER PUBLICATIONS

The Machine translated document of FR2931066.*

* cited by examiner

*Primary Examiner* — Ernst Arnold
*Assistant Examiner* — Kauser M Akhoon
(74) *Attorney, Agent, or Firm* — Novak Druce Connolly Bove + Quigg LLP

(57) ABSTRACT

The present invention relates to the use of at least one piperidine ester derivative of formula (I) below: in which: $R_1$ is a linear or branched $C_1$-$C_{12}$ alkyl radical, $R_2$ is a linear or branched $C_1$-$C_{20}$ alkyl radical, with the proviso that the sum of the carbon atoms for $R_1$ and $R_2$ is between 2 and 22, in a composition comprising, in a cosmetically acceptable medium, at least one liquid fatty phase and at least one lipophilic active agent, and containing no dibenzoylmethane-type UV screening agent, as a solvent for said active agent in said liquid fatty phase and/or as an agent improving the solubility of said active agent in said fatty phase. The present invention also relates to a composition comprising, in a cosmetically acceptable medium, at least one liquid fatty phase, characterized in that it comprises at least one piperidine ester derivative of formula (I) as defined above and in that it does not contain a dibenzoylmethane-type UV screening agent.

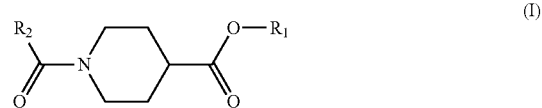

(I)

23 Claims, No Drawings

USE OF PIPERIDINE ESTER DERIVATIVE AS SOLVENT IN COSMETIC COMPOSITIONS; COSMETIC COMPOSITIONS COMPRISING IT

CROSS REFERENCE TO RELATED APPLICATIONS

This application is a National Phase filing under 35 U.S.C. §371 of PCT/EP2009/062817 filed on Oct. 2, 2009; the entire contents of all are hereby incorporated by reference.

The present invention relates to the use of at least one specific piperidine ester derivative of formula (I), whose definition will be given hereinafter, in a composition comprising, in a cosmetically acceptable medium, at least one liquid fatty phase and at least one lipophilic active agent, and containing no dibenzoylmethane-type UV screening agent, as a solvent for said active agent in said liquid fatty phase and/or as an agent improving the solubility of said active agent in the solid fatty phase.

The present invention is concerned more particularly with a composition comprising, in a cosmetically acceptable medium, at least one liquid fatty phase, characterized in that it comprises at least one specific piperidine ester derivative of formula (I) and at least one lipophilic active agent and does not contain a dibenzoylmethane-type UV screening agent.

Many cosmetic or dermatological products are provided in various formulating forms comprising a liquid fatty phase, such as dispersions, oily lotions, oil/water, water/oil or multiple emulsions, or cream gels. Certain cosmetic or dermatological active agents that are particularly advantageous, such as lipophilic organic screening agents that are not readily soluble in the oily phase of these formulations, have a tendency, during storage, to form crystals or to precipitate, in particular in emulsions. Such phenomena are undesirable from the point of view of stability of the formulation and/or with respect to consumer comfort, insofar as they can destabilize the composition and/or affect the aesthetic appearance of the product and/or lead to cosmetic discomfort upon application to the skin and/or the hair, or else to the concentration of active agents being limited in these formulas, which means that products that are sufficiently effective cannot be obtained.

This is the case in particular of care formulations containing low-solubility lipophilic active agents such as the active agents chosen from aminophenol derivatives, salicylic acid derivatives, 2-amino-4-alkylaminopyrimidine 3-oxide derivatives, in particular 2-amino-4-dodecylaminopyrimidine 3-oxide, DHEA (dehydroepiandrosterone), chemical derivatives and precursors thereof, such as 7-hydroxy- or 7-keto-DHEA, or else 3β-acetoxy-7-keto-DHEA, cholesterol and esters thereof, plant sterols such as phytosterols and sitosterols and esters thereof, pentacyclic triterpene acids, hydroxystilbenes, flavonoids, lipophilic organic UV screening agents in antisun formulations, retinol and derivatives thereof, carotenoids such as lycopene, and also fragrances, essential oils, hormones, vitamins, in particular vitamin E, ceramides, or mixtures thereof.

In particular, antisun compositions are often in the form of an oil-in-water or water-in-oil emulsion, of gels or of anhydrous products which contain, at various concentrations, one or more lipophilic and/or hydrophilic, insoluble and/or soluble, organic and/or inorganic screening agents, capable of selectively absorbing harmful UV radiation. These screening agents and the amounts thereof are selected according to the desired protection factor. Depending on whether they are lipophilic or, conversely, hydrophilic in nature, these screening agents can disperse, respectively, either into the fatty phase or into the aqueous phase of the final composition.

Lipophilic screening agents are in common use in suncare formulations. For some of them, however, their photoprotective power when formulated is quite limited in the usual cosmetic carriers containing oils, such as oxyethylenated or oxypropylenated fatty (mono/poly) alcohols ("Cetiol HE" from Henkel or "Witconol APM" from Witco) or else fatty esters such as $C_{12}$-$C_{15}$ alcohol benzoate ("Finsolv TN" from Finetex), fatty acid triglycerides, for example Miglyol® 812 sold by the company Dynamit Nobel, or amino acid derivatives ("Eldew SL205" from Ajinomoto), because the solubility of these screening agents when formulated in these commonly used oils is insufficient. The result of this is: either the appearance over time of crystallization in the formulas, which is detrimental to the good quality, stability and effectiveness of the antisun products; or the fact that the concentration of screening agents in the formulas has to be limited, thereby making it impossible to obtain sufficiently effective products.

There exists therefore the need to find novel solvents for effectively dissolving lipophilic active agents and especially lipophilic screening agents in order to enhance their solubility in the oils and the carriers of cosmetic or dermatological formulations containing them, without the drawbacks listed above.

It is known that certain piperidine ester derivatives have been used as a light stabilizer agent for dibenzoylmethane-type UV screening agents, from unpublished French Patent Application No. 0853107.

Now, the applicant has just discovered, surprisingly, a new family of effective solvents consisting of specific piperidine ester derivatives of formula (I), the definition of which will be given hereinafter, which make it possible to achieve this objective. These compounds can be incorporated into many cosmetic products.

This discovery forms the basis of the present invention.

The present invention relates to the use of at least one specific piperidine ester derivative of formula (I), whose definition will be given hereinafter, in a composition comprising, in a cosmetically acceptable medium, at least one liquid fatty phase and at least one lipophilic active agent, and containing no dibenzoylmethane-type UV screening agent, as a solvent for said active agent in said liquid fatty phase and/or as an agent improving the solubility of said active agent in said fatty phase.

The present invention is concerned more particularly with a composition comprising, in a cosmetically acceptable medium, at least one liquid fatty phase, characterized in that it comprises at least one specific piperidine ester derivative of formula (I) and at least one lipophilic active agent and in that it does not contain a dibenzoylmethane-type UV screening agent.

The present invention also relates to the use of at least one piperidine ester derivative of formula (I) in a composition comprising, in a cosmetically acceptable medium, at least one liquid fatty phase and at least one lipophilic active agent, and containing no dibenzoylmethane-type UV screening agent, for the purpose of improving the effectiveness of said active agent and/or the cosmetic qualities and/or the stability of said composition.

The present invention likewise relates to the use of at least one piperidine ester derivative of formula (I) in a composition comprising, in a cosmetically acceptable medium, at least one liquid fatty phase and at least one organic UV screening agent, and containing no dibenzoylmethane-type UV screening agent, for the purpose of improving the sun protection factor.

Other characteristics, aspects and advantages of the invention will become apparent upon reading the detailed description which follows.

The term "cosmetically acceptable" is intended to mean compatible with the skin and/or its epidermal derivatives, which has a pleasant colour, smell and feel and which does not generate any unacceptable discomfort (stinging, tautness, redness) that may dissuade the consumer from using this composition.

For the purpose of the present invention, the term "liquid fatty phase" is intended to mean a fatty phase which is liquid at ambient temperature (25° C.) and atmospheric pressure (760 mmHg), composed of one or more fatty substances that are liquid at ambient temperature, also known as oils, and that are compatible with one another.

The term "lipophilic active agent" is intended to mean any cosmetic or dermatological active agent that is capable of being completely dissolved in the molecular state in a liquid fatty phase or else of being solubilized in colloidal form (for example, in micellar form) in a liquid fatty phase.

The term "low-solubility lipophilic active agent" is intended to mean any organic cosmetic or dermatological active agent which has a solubility in water of less than 0.5% by weight and a solubility of less than 10% by weight in the majority of organic solvents such as liquid paraffin, fatty alcohol benzoates and fatty acid triglycerides, for example Miglyol® 812 sold by the company Dynamit Nobel. This solubility, realized at 70° C., is defined as being the amount of product in solution in the solvent at equilibrium with an excess of solid in suspension after a return to ambient temperature. It can be readily evaluated in the laboratory.

The piperidine ester compounds of formula (I) in accordance with the invention are chosen from those corresponding to general formula (I) below:

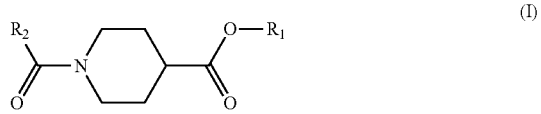

(I)

in which:

$R_1$ is a linear or branched $C_1$-$C_{12}$ alkyl radical, $R_2$ is a linear or branched $C_1$-$C_{20}$ alkyl radical, with the proviso that the sum of the carbon atoms for $R_1$ and $R_2$ is between 2 and 22.

Among the compounds of formula (I), use will be made more particularly of the compounds (a) to (c) below:

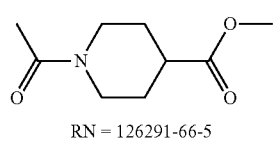

(a)

RN = 126291-66-5

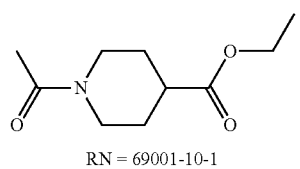

(b)

RN = 69001-10-1

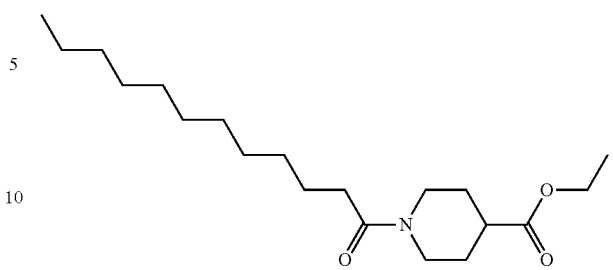

(c)

The piperidine ester compounds of formula (I) in accordance with the invention are known per se and may be prepared by the process which is described widely in the literature.

The process generally used for preparing compounds of formula (I) is the following process, represented by the reaction scheme below.

The compound (II) (ester of 4-piperidine carboxylic acid) is acylated by reaction with an acid chloride of formula (III) or the anhydride of formula (IV). The compound (I) is obtained by distillation of the crude reaction product.

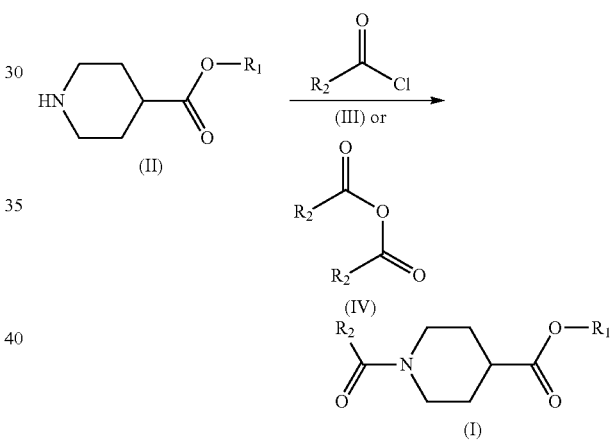

The radicals $R_1$ and $R_2$ have the same definitions as in the formula (I) indicated above.

In one particular form of the invention, the derivative or derivatives of formula (I) in accordance with the invention are present in an amount sufficient to solubilize by itself or by themselves (without the need to use another solvent) the total amount of lipophilic active agent(s) present in the composition.

According to another particular form of the invention, the derivative or derivatives of formula (I) in accordance with the invention constitute the sole solvent of the lipophilic active agent(s). In that case the liquid fatty phase may be composed of the derivative or derivatives of formula (I) and the lipophilic active agent or agents dissolved in said phase.

Among the lipophilic active agents which can be used in accordance with the invention, use will be made of lipophilic organic UV screening agents. They may be selected from para-aminobenzoic acid derivatives, salicylic derivatives, cinnamic derivatives, benzophenones and aminobenzophenones, anthranillic derivatives, β,β-diphenylacrylate derivatives, benzylidenecamphor derivatives, phenylbenzimidazole derivatives, benzotriazole derivatives, triazine derivatives, bisresorcinyl triazines, imidazoline derivatives, benzalmalonate derivatives, 4,4-diarylbutadiene derivatives, benzoxazole derivatives, merocyanines, malonitrile or malonate diphenyl butadiene derivatives, chalcones and mixtures thereof.

The lipophilic UVA screening agents, which are capable of absorbing the UV radiation from 320 to 400 nm, include the following:

Aminobenzophenones
n-Hexyl 2-(4-diethylamino-2-hydroxybenzoyl)-benzoate, sold under the trade name Uvinul A+.

Anthranillic Derivatives
Menthyl anthranilate, sold under the trade name Neo Heliopan MA by Haarmann and Reimer.

4,4-Diarylbutadiene Derivatives
1,1-dicarboxy(2,2'-dimethylpropyl)-4,4-diphenyl-butadiene. Those preferred are:

The lipophilic UVB screening agents, which are capable of absorbing the UV radiation from 280 to 320 nm, include:

para-Aminobenzoates
Ethyl PABA
Ethyl dihydroxypropyl PABA
Ethylhexyl dimethyl PABA (Escalol 507 from ISP)

Salicylic Derivatives
Homosalate, sold under the name Eusolex HMS by Rona/EM Industries,
Ethylhexyl salicylate, sold under the name Neo Heliopan OS by Haarmann and Reimer,
Dipropylene glycol salicylate, sold under the name Dipsal by Scher,
TEA salicylate, sold under the name Neo Heliopan TS by Haarmann and Reimer.

Cinnamates
Ethylhexyl methoxycinnamate, sold in particular under the trade name Parsol MCX by Hoffmann La Roche,
Isopropyl methoxy cinnamate,
Isoamyl methoxy cinnamate, sold under the trade name Neo Heliopan E 1000 by Haarmann and Reimer,
Diisopropyl methylcinnamate,
Cinoxate,
Glyceryl ethylhexanoate dimethoxycinnamate.

β,β'-Diphenylacrylate Derivatives
Octocrylene, sold in particular under the trade name Uvinul N539 by BASF,
Etocrylene, sold in particular under the trade name Uvinul N35 by BASF.

Benzylidenecamphor Derivatives
3-Benzylidenecamphor, manufactured under the name Mexoryl SD by Chimex,
Methylbenzylidenecamphor, sold under the name Eusolex 6300 by Merck,
Polyacrylamidomethyl benzylidenecamphor, manufactured under the name Mexoryl SW by Chimex.

Triazine Derivatives
Ethylhexyl triazone, sold in particular under the trade name Uvinul T150 by BASF,
Diethylhexyl butamido triazone, sold under the trade name Uvasorb HEB by Sigma 3V,
2,4,6-tris(dineopentyl 4'-aminobenzalmalonate)-s-triazine,
2,4,6-tris(diisobutyl 4'-aminobenzalmalonate)-s-triazine,
2,4-bis(dineopentyl 4'-aminobenzalmalonate)-6-(n-butyl 4'-aminobenzoate)-s-triazine,
2,4-bis(n-butyl 4'-aminobenzoate)-6-(aminopropyl-trisiloxane)-s-triazine.

Imidazoline Derivatives
Ethylhexyl dimethoxybenzylidene dioxoimidazoline propionate.

Benzalmalonate Derivatives
Polyorganosiloxanes with benzalmalonate function, such as Polysilicon-15, sold under the trade name Parsol SLX by Hoffmann La Roche,
Dineopentyl 4'-methoxybenzalmalonate.

Merocyanine Derivatives
Octyl 5-N,N-diethylamino-2-phenylsulphonyl-2,4-pentadienoate.

Broad-spectrum lipophilic screening agents, which are capable of absorbing both UVA and UVB radiation, include the following:

Benzophenone Derivatives
Benzophenone-1, sold under the trade name Uvinul 400 by BASF,
Benzophenone-2, sold under the trade name Uvinul D50 by BASF,
Benzophenone-3 or oxybenzone, sold under the trade name Uvinul M40 by BASF,
Benzophenone-5,
Benzophenone-6, sold under the trade name Helisorb 11 by Norquay,
Benzophenone-8, sold under the trade name Spectra-Sorb UV-24 by American Cyanamid,
Benzophenone-10,
Benzophenone-11,
Benzophenone-12.

Benzotriazole Derivatives
Drometrizole trisiloxane, sold under the name Silatrizole by Rhodia Chimie,
Bumetrizole, sold under the name Tinoguard AS by Ciba-Geigy.

Bisresorcinyl Triazine Derivatives
Bisethylhexyloxyphenol methoxyphenyl triazine, sold under the trade name Tinosorb S by Ciba Geigy.

Benzoxazole Derivatives
2,4-Bis[5-(dimethylpropyl)benzoxazol-2-yl(4-phenyl)imino]-6-(2-ethylhexyl)imino-1,3,5-triazine, sold under the name Uvasorb K2A by Sigma 3V.

The derivatives from the class of the malonitrile or malonate diphenyl butadienes are derivatives of general formula (IV):

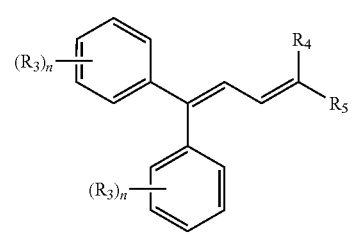

in which $R_3$ represents a $C_1$-$C_2$ alkyl group or a $C_1$-$C_2$ alkoxy group and n is 0, 1 or 2;

$R_4$ and $R_5$, which are identical or different, represent —COOR$_6$, —(C=O)NHR$_6$, —(C=O)R$_6$ or —CN, in which $R_6$ represents an alkyl group containing 1 to 12 carbon atoms which is linear or branched and may contain silane, siloxane or polysiloxane groups.

The malonitrile or malonate diphenyl butadiene derivatives include more particularly, without limitation:
dimethyl 2-(3,3-diphenylprop-2-enylidene)malonate
diisobutyl 2-(3,3-diphenylprop-2-enylidene)malonate
bis(1,3-dimethylbutyl) 2-(3,3-diphenylprop-2-enylidene) malonate
dineopentyl 2-(3,3-diphenylprop-2-enylidene)malonate
methyl (2Z)-2-cyano-5,5-diphenylpenta-2,4-dienoate
ethyl(trimethylsilyl)methyl (2Z)-2-(3,3-diphenyl-prop-2-enylidene)malonate
(2E)-2-cyano-5,5-diphenyl-N-(3-{1,3,3,3-tetramethyl-1-[(trimethylsilyl)oxy]disiloxanyl}propyl)penta-2,4-dienamide
ethyl 2-methyl-3-{1,3,3,3-tetramethyl-1-[(trimethyl-silyl)oxy]disiloxanyl}propyl (2E)-2-(3,3-diphenylprop-2-enylidene) malonate
ethyl (2Z)-5,5-diphenyl-2-{[(3-{1,3,3,3-tetramethyl-1-[(trimethylsilyl)-oxy]disiloxanyl}propyl)amino]-carbonyl}penta-2,4-dienoate Among the abovementioned diphenyl butadiene derivatives, use will be made in particular of dineopentyl 2-(3,3-diphenylprop-2-enylidene)malonate, corresponding to the formula below:

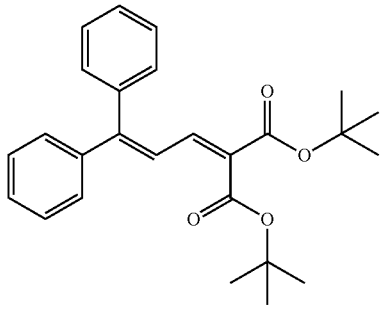 [SMILES: CC(C)(C)OC(=O)C(=CC=C(c1ccccc1)c1ccccc1)C(=O)OC(C)(C)C]

It is known to use these diphenyl butadiene derivatives in suncare compositions: patent EP 0916335 describes carbon derivatives and also methods of obtaining them, and patents EP 1535947 and EP 1535925 describe siloxane and silane derivatives, respectively.

The derivatives from the class of the chalcones are derivatives of general formula (V) below:

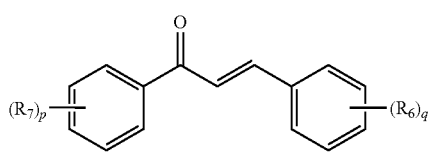

in which the radicals $R_6$ and $R_7$ are, independently of one another, a hydrogen atom, the hydroxyl radical, a linear or branched $C_1$-$C_{12}$ alkyl or alkenyl group, a linear or branched $C_1$-$C_{12}$ alkoxy group or a linear or branched $C_2$-$C_{20}$ acyloxy group;
p and q The chalcone derivatives more particularly include, without limitation:
2'-hydroxychalcone
4'-hydroxychalcone
4'-methoxychalcone
2'-hydroxy-4-methoxychalcone
2'-hydroxy-4-hexyloxychalcone
2'-hydroxy-4-methylchalcone
2'-hydroxy-3-hexyloxychalcone
2'-hydroxy-4'-hexyloxy-4-methylchalcone
2'-hydroxy-4'-hexanoyloxy-4-methoxychalcone
2',4',4-trihydroxy-3,3'-diallylchalcone (known under the name Kazonol)
2',4',4-trihydroxy-5'-(3-methylbut-2-ene)chalcone (known under the name Broussochalcone B)
2',3',4',6',4-pentahydroxychalcone (known under the name Carthamin).

Of the aforementioned chalcone derivatives, use will be made in particular of 4'-hydroxychalcone, corresponding to formula (Va) below:

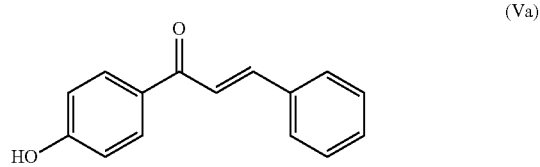 [SMILES: O=C(/C=C/c1ccccc1)c1ccc(O)cc1]

or else of 2',3',4',6',4-pentahydroxychalcone (known under the name Carthamin), corresponding to formula (Vb) below:

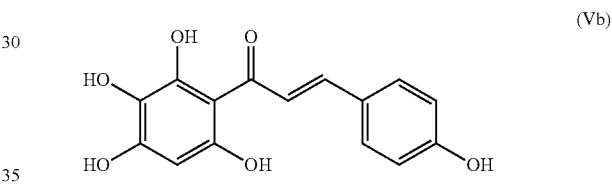

It is known to use these chalcone derivatives in suncare compositions, particularly from patents FR 2555167, FR 2602228 and FR 2608150.

The lipophilic screening agents are generally present in the compositions according to the invention in proportions of from 0.01% to 20% by weight, relative to the total weight of the composition, and preferably of from 0.1% to 10% by weight, relative to the total weight of the composition.

Among the lipophilic screening agents whose lipophilicity is difficult, mention may be made, for example, of dibenzoylmethane derivatives, triazines, merocyanines, benzotriazoles, chalcones, benzophenones or aminobenzophenones, and the derivatives from the class of the malonitrile or malonate diphenyl butadienes.

The term "low-solubility lipophilic screening agent" is intended to mean any organic cosmetic or dermatological active agent which has a solubility in water of less than 0.5% by weight and a solubility of less than 10% by weight in the majority of organic solvents such as liquid paraffin, fatty alcohol benzoates and fatty acid triglycerides, for example Miglyol® 812 sold by the company Dynamit Nobel. This solubility, realized at 70° C., is defined as being the amount of product in solution in the solvent at equilibrium with an excess of solid in suspension after a return to ambient temperature. It can be readily evaluated in the laboratory.

The low-solubility lipophilic active agents in accordance with the invention may also be selected from aminophenol derivatives, salicylic acid derivatives, N,N'-di(arylmethylene)ethylenediaminetriacetate derivatives, 2-amino-4-alkylaminopyrimidine 3-oxide derivatives, flavonoids, retinol and derivatives thereof, carotenoids such as lycopene, and also fragrances, essential oils, hormones, vitamins, especially vitamin E, ceramides, or mixtures thereof.

The aminophenol derivatives used are more particularly the derivatives of formula (1) below:

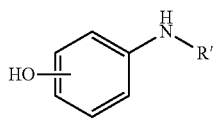

(1)

in which R' is a radical chosen from the group made up of the following radicals (a), (b) and (c):
(a) —CO—NR$^1$R$^2$
(b) —CO—O—R$^3$
(c) —SO$_2$R$^3$
where R$^1$ represents a hydrogen atom or an optionally hydroxylated, saturated or unsaturated, linear or branched C$_1$ to C$_6$ alkyl radical,
R$^2$ represents a hydrogen atom or a radical chosen from saturated or unsaturated, linear, cyclic or branched C$_{12}$ to C$_{30}$ alkyl radicals, which is optionally hydroxylated, and
R$^3$ represents a radical chosen from saturated or unsaturated, linear, cyclic or branched, including fused polycyclic, C$_{12}$ to C$_{30}$ alkyl radicals, which are optionally hydroxylated.

In formula (1), among the linear or branched R$^2$ or R$^3$ radicals containing from 1 to 30 carbon atoms, mention may advantageously be made of methyl, ethyl, propyl, isopropyl, butyl, tert-butyl, hexyl, octyl, nonyl, 2-ethylhexyl, dodecyl, hexadecyl, behenyl, octadecyl and 2-butyloctyl radicals. These radicals preferably contain from 1 to 12 carbon atoms. Even more preferably, the alkyl radical generally contains from 1 to 6 carbon atoms. As a lower alkyl radical, mention may be made of methyl, ethyl, propyl, isopropyl, tert-butyl and hexyl radicals.

When it is unsaturated, a radical having one or more ethylenic unsaturations, such as more particularly the allyl radical, is preferred.

When the alkyl radical is cyclic, mention may in particular be made of the cyclohexyl, cholesteryl or tert-butylcyclohexyl radical.

When it is hydroxylated, the radical preferably contains from 1 to 6 carbon atoms and from 1 to 5 hydroxyl groups. Among monohydroxyalkyl radicals, a radical preferably containing 1 or 3 carbon atoms, in particular the hydroxymethyl, 2-hydroxyethyl, 2-hydroxypropyl or 3-hydroxypropyl radical, is preferred.

Among polyhydroxyalkyl radicals, a radical containing from 3 to 6 carbon atoms and from 2 to 5 hydroxyl groups, such as the 2,3-dihydroxypropyl, 2,3,4-trihydroxybutyl, 2,3,4,5-tetrahydroxypentyl or 2,3,4,5,6-pentahydroxyhexyl radical, is preferred.

The alkoxylated radicals are alkyl radicals, as in particular described above, preceded by an oxygen atom.

Preferably, the aminophenol derivatives used in the present application are those for which at least one and preferably all of the conditions below are met:
the —OH function on the phenyl radical is in the ortho-position or, advantageously, in the para-position,
R' is chosen from a radical of formulae (a) or (b).

Among the linear or branched alkyl radicals R$^1$, mention may be made of methyl, ethyl, propyl, isopropyl, tert-butyl or hexyl radicals.

The aminophenol derivative preferably used in said composition is a para-aminophenol derivative; even more preferably, it is N-ethoxycarbonyl-4-para-aminophenol of formula (1a):

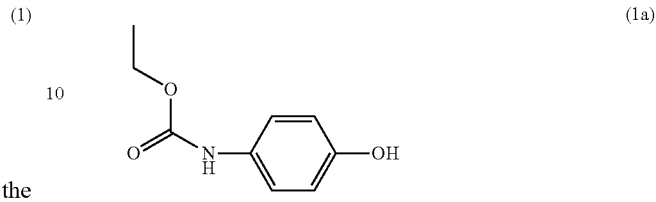

(1a)

or else N-cholesteryloxycarbonyl-4-para-aminophenol of formula (1b):

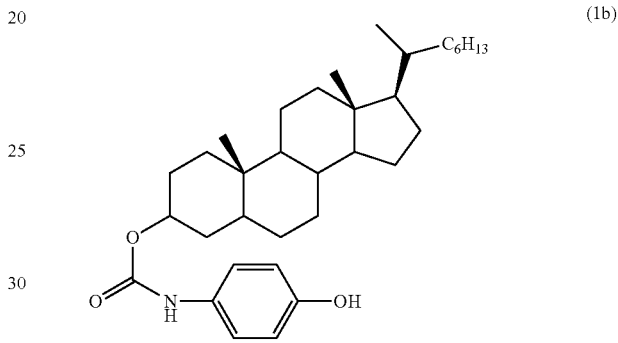

(1b)

These aminophenol derivatives, and the process for preparing them, are described in Patent Applications WO 99/10318 and WO 99/32077.

These derivatives have a more or less long hydrocarbon chain, preferably alkoxycarbonyl chain, attached to the nitrogen atom. They have the drawback of being soluble poorly, or even not at all, in water or in the fatty phase of the type used in the present application. Their introduction into cosmetic compositions requires, as regards the compounds with a short hydrocarbon chain, them to be solubilized in an aqueous-alcoholic solution, which is not always desirable when the composition is intended, for example, to be applied around the eyes.

As for the compounds with a long hydrocarbon chain, they are insoluble in oils, owing to their steric bulk, and have a tendency to recrystallize from water.

The compositions according to the present invention comprising such an aminophenol derivative can be used as a depigmenting or bleaching agent in a cosmetic and/or dermatological composition.

The salicylic acid derivatives are the derivatives of formula (2):

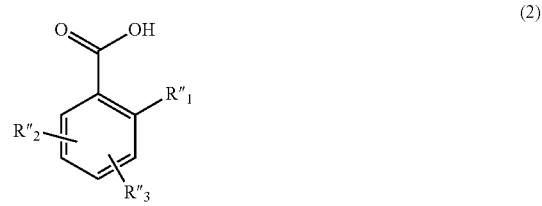

(2)

in which

R″$_1$ represents a hydroxyl radical or an ester of formula

—O—CO—R″$_4$ in which R″$_4$ is a saturated or unsaturated aliphatic radical containing from 1 to 26 carbon atoms, and preferably from 1 to 18 carbon atoms, or an amine or thiol function optionally substituted with an alkyl radical containing from 1 to 18 carbon atoms, and preferably from 1 to 12 carbon atoms, R″$_2$ and R″$_3$, independently of one another, are in the 3-, 4-, 5- or 6-position on the benzene ring and represent, independently of one another, a hydrogen atom or a radical:

—(O)$_n$—(CO)$_m$—R″$_5$ in which n and m, independently of one another, are each an integer equal to 0 or 1, provided that R″$_2$ and R″$_3$ are not simultaneously hydrogen atoms, and R″$_5$ represents a hydrogen, a linear, branched or cyclized, saturated aliphatic radical containing from 1 to 18 carbon atoms, or an unsaturated radical containing from 3 to 18 carbon atoms, bearing one to nine conjugated or unconjugated double bonds, it being possible for the radicals to be substituted with at least one substituent chosen from halogen atoms (fluorine, chlorine, bromine or iodine), the following radicals: trifluoromethyl, hydroxyl in free form or esterified with an acid containing from 1 to 6 carbon atoms, or carboxyl in free form or esterified with a lower alcohol containing from 1 to 6 carbon atoms, or an aromatic radical containing from 6 to 10 carbon atoms.

Preferably, the salicylic acid derivative is such that R″$_5$ represents a saturated aliphatic radical containing from 3 to 15 carbon atoms.

Preferably, the salicylic acid derivative is such that R″$_1$ represents a hydroxyl radical.

Preferably, the salicylic acid derivative is such that R″$_5$ is in the 5-position on the benzene ring and R″$_2$ represents a hydrogen atom.

According to a preferred embodiment of the invention, the salicylic acid derivatives are derivatives of 5-n-octanoylsalicylic acid, 5-n-decanoylsalicylic acid, 5-n-dodecanoylsalicylic acid, 5-n-octylsalicylic acid, 5-n-heptyloxysalicylic acid, 4-n-heptyloxysalicylic acid, 5-tert-octylsalicylic acid, 3-tert-butyl-5-methylsalicylic acid, 3-tert-butyl-6-methylsalicylic acid, 3,5-diisopropylsalicylic acid, 5-butoxysalicylic acid, 5-octyloxysalicylic acid, 5-propanoylsalicylic acid, 5-n-hexadecanoylsalicylic acid, 5-n-oleoylsalicylic acid, 5-benzoylsalicylic acid, monovalent and divalent salts thereof, and mixtures thereof.

Very particular preference is given to employing the 2-hydroxy-5-octanoylbenzoic acid available for sale under the trade name Mexoryl SAB by the company Chimex; it corresponds to the following formula:

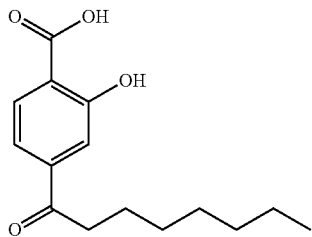 [SMILES: CCCCCCCC(=O)c1ccc(C(=O)O)c(O)c1]

It is known practice to use salicylic acid derivatives in topical compositions, for example, as a keratolytic agent for treating acne or as an anti-ageing agent; Patent Applications FR-A-2 581 542 and EP-A-378 936 describe such derivatives.

Salicylic acid derivatives are highly advantageous in particular for preventing or repairing the principal manifestations of skin ageing, namely fine lines and wrinkles, disruption of the "grain" of the skin, modification of the complexion of the skin and loss of firmness and of tonicity of the skin. However, the use of these derivatives poses a problem insofar as, when they are introduced without modification into topical compositions, they do not solubilize and remain in the crystalline state, rendering the use of the composition containing them ineffective for the treatment of the skin.

Generally, these derivatives are solubilized in lower alcohols, such as ethanol or isopropanol, or solvents such as octyldodecanol, certain glycols, or short-chain (less than $C_{12}$) fatty alcohols. However, these lower alcohols have the drawback of drying out and irritating the skin; it is therefore preferred to avoid using them in body and/or facial care products. In addition, these solubilizing agents can only be introduced in small amounts otherwise they may impair the cosmetic qualities (drying out of the skin) and the stability of the compositions containing them.

The concentration of salicylic acid derivatives of the composition according to the present invention is preferably from 0.001% to 15% by weight, more preferably from 0.1% to 5% by weight, relative to the total weight of the composition. The amount of amino acid esters will depend on the amount of salicylic acid derivatives to be solubilized. It may be from 0.01% to 90% by weight, and preferably between 0.1% and 60% by weight, relative to the total weight of the composition.

The composition according to the invention comprising at least one salicylic derivative can be used as a cosmetic or dermatological composition, and in particular for caring for, protecting, cleansing and/or making up keratin materials of human beings (skin, lips, keratin fibres such as the hair and eyelashes), and in particular for combating the signs of skin ageing and/or for smoothing facial and/or body skin and/or for treating wrinkles and fine lines of the skin and/or for stimulating the process of epidermal renewal and/or for depigmenting or bleaching the skin and/or for treating acne and/or for treating skin disorders.

These derivatives and their preparation process are described in patent WO 94/11338.

The derivatives of the 2-amino-4-alkylamino-pyrimidine 3-oxide family are the derivatives of general formula (3):

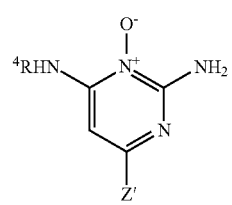

(3)

in which $R^4$ represents an alkyl group containing from 1 to 20 carbon atoms, and Z' represents a hydrogen atom or an —OR$^5$ radical in which $R^5$ represents an alkyl group containing from 1 to 12 carbon atoms, and also its acylated forms or its addition salts with acids.

Preferably, $R^4$ is chosen from the group made up of hexyl, heptyl, octyl, nonyl, decyl, undecyl and dodecyl radicals.

Preferably, $R^5$ is chosen from the group made up of ethyl, propyl, butyl, pentyl and hexyl radicals.

More preferably, the compound is 2-amino-4-dodecylaminopyrimidine 3-oxide.

The derivatives of the 2-amino-4-alkylaminopyrimidine 3-oxide family can in particular be used in or for the preparation of a cosmetic or dermatological composition in accordance with the present invention for preventing and treating problems associated with sensitive skin and skin disturbances such as skin discomfort, tautness of the skin, skin itching, skin swelling, redness of the skin and heat sensation of the skin.

Another family of molecules which comes under the definition of molecules with low water-solubility is DHEA, its derivatives and its chemical or metabolic precursors.

DHEA, or dehydroepiandrosterone, also known as 3-beta-hydroxyandrost-5-en-17-one, or dehydroiso-androsterone, but also trans-dehydroandrosterone or prasterone, has the formula:

[Chemical structure]

The expression "DHEA precursors to which the invention relates" is intended to mean its biological precursors which are capable of being converted to DHEA during metabolism, and also its chemical precursors which can be converted to DHEA by exogenous chemical reaction.

Examples of biological precursors are Δ5-pregnenolone, 17α-hydroxypregnenolone and 17α-hydroxypregnenolone sulphate, without this list being limiting.

The expression "chemical precursors of DHEA" is intended to mean in particular saponins and their derivatives such as hecogenin ((3beta, 5alpha, 23r)-3-hydroxyspirostan-12-one) and hecogenin acetate, diosgenin (5-spirosten-3-beta-ol), smilagenin and sarsapogenin, and also natural extracts containing them, in particular fenugreek and extracts of Dioscorea plants such as wild yam root, without this list being limiting.

The term "DHEA derivatives" is intended to mean both its metabolic derivatives and its chemical derivatives. As metabolic derivatives, mention may in particular be made of Δ5-androstene-3,17-diol, and in particular 5-androstene-3β, 17β-diol, Δ4-androstene-3,17-dione, 7-hydroxy-DHEA (7α-hydroxy-DHEA or 7β-hydroxy-DHEA) and 7-keto-DHEA, which is itself a metabolite of 7β-hydroxy-DHEA, without this list being limiting.

7α-Hydroxy-DHEA is, with 5-androstene-3β, 17β-diol, a major metabolite of DHEA, obtained by the action of 7α-hydroxylase on DHEA. 7β-Hydroxy-DHEA is a minor metabolite of DHEA, obtained by the action of 7β-hydroxylase on DHEA.

The 7-hydroxy-DHEA preferably used in the compositions according to the present invention is 7α-hydroxy-DHEA. A process for preparing this compound is described in Patent Applications FR 2 771 105 and WO 94/08588.

As chemical derivatives of DHEA, mention may also be made of DHEA salts, and in particular water-soluble salts such as DHEA sulphate; DHEA esters such as esters of hydrocarboxylic acids and of DHEA, in particular those described in U.S. Pat. No. 5,736,537, or else DHEA salicylate, DHEA acetate, DHEA valerate (or n-heptanoate) and DHEA enanthate.

Mention may also be made of DHEA carbamates, 2-hydroxymalonate esters of DHEA and amino acid esters of DHEA. Finally, mention may be made of 3β-acetoxy-7-oxo-DHEA which can in particular be prepared as described in U.S. Pat. No. 5,869,709 and U.S. Pat. No. 6,111,118. This list is obviously not limiting.

The concentration of DHEA-based compound in the composition according to the present invention can advantageously range from 0.001% to 30% by weight, preferably from 0.01% to 20%, and even more preferably from 0.01% to 10% by weight, relative to the total weight of the composition. These compounds will be in solubilized form between 20° C. and 90° C.

According to a specific embodiment of the invention, the derivative(s) of formula (I) in accordance with the invention is (are) used as sole solvent for said lipophilic active agent(s).

The compositions in accordance with the invention may also comprise other organic UV screening agents that are active in the UVA range and/or the UVB range and that are water-soluble or else insoluble in the cosmetic solvents commonly used.

The water-soluble UVA screening agents, which are capable of absorbing the UV radiation from 320 to 400 nm, include terephthalylidene dicamphor sulphonic acid, manufactured under the name Mexoryl SX by Chimex, bisbenzoazolyl derivatives such as those described in patents EP 669 323 and U.S. Pat. No. 2,463,264, and more particularly the compound disodium phenyl dibenzimidazole tetrasulphonate, sold under the commercial trade name Neo Heliopan AP by Haarmann and Reimer.

The water-soluble UVB screening agents, which are capable of absorbing the UV radiation from 280 to 320 nm, include p-aminobenzoic acid (PABA) derivatives such as:

PABA,

Glyceryl PABA, and

PEG-25 PABA, sold under the name Uvinul P25 by BASF,

Phenylbenzimidazole sulphonic acid, sold in particular under the trade name Eusolex 232 by Merck, Ferulic acid, Salicylic acid, DEA methoxycinnamate, Benzylidene camphor sulphonic acid, manufactured under the name Mexoryl SL by Chimex, Camphor benzalkonium methosulphate, manufactured under the name Mexoryl SO by Chimex, and The water-soluble UVA and UVB screening agents include:

Benzophenone-4, sold under the trade name Uvinul MS40 by BASF,

Benzophenone-5, and

Benzophenone-9.

The insoluble screening agents include:

methylene bisbenzotriazolyl tetramethylbutylphenol, sold in solid form under the trade name Mixxim BB/100 by Fairmount Chemical or in micronized form in aqueous dispersion under the trade name Tinosorb M by Ciba Specialty Chemicals, the symmetrical triazine screening agents described in U.S. Pat. No. 6,225,467, patent application WO 2004/085412 (see compounds 6 and 9) or the document "Symmetrical Triazine Derivatives", IP.COM Journal, IP.COM INC., West Henrietta, N.Y., US (20 Sep. 2004), more particularly the 2,4,6-tris (biphenyl)-1,3,5-triazines (especially 2,4,6-tris(biphenyl-4-yl)-1,3,5-triazine) and 2,4,6-tris(terphenyl)-1,3,5-triazine, which is included in the Beiersdorf patent applications WO 06/035000, WO 06/034982, WO 06/034991, WO 06/035007, WO 2006/034992, WO 2006/034985.

Of course, those skilled in the art will take care to select the optional additional screening agents and/or the amounts thereof in such a way that the advantageous properties intrinsically associated with the compositions in accordance with the invention are not, or are not substantially, impaired by the addition(s) envisaged.

The compositions according to the invention may also contain artificial tanning and/or browning agents for the skin (self-tanning agents) and more particularly dihydroxyacetone (DHA). They are preferably present in amounts ranging from 0.1 to 10% by weight relative to the total weight of the composition.

The aqueous compositions conforming to the present invention may moreover comprise conventional cosmetic adjuvants in particular chosen from fatty substances, organic solvents, ionic or non-ionic, hydrophilic or lipophilic thickeners, demulcents, humectants, opacifiers, stabilizers, emollients, silicones, anti-foaming agents, fragrances, preservatives, anionic, cationic, non-ionic, zwitterionic or amphoteric surfactants, active agents, fillers, polymers, propellants and basifying or acidifying agents, or any other ingredient commonly used in the cosmetics and/or dermatological field.

The fatty substances may be composed of an oil or a wax other than the apolar waxes as defined previously, or mixtures thereof. The term "oil" is understood to mean a compound which is liquid at ambient temperature. The term "wax" is understood to mean a compound which is solid or substantially solid at ambient temperature, and of which the melting point is generally greater than 35° C.

As oils, mention may be made of mineral oils (paraffin); vegetable oils (sweet almond oil, macadamia oil, blackcurrant seed oil, jojoba oil); synthetic oils such as perhydrosqualene, alcohols, fatty amides (such as isopropyl lauroyl sarcosinate sold under the name "Eldew SL-205" by Ajinomoto), fatty acids or esters such as the benzoate of $C_{12}$-$C_{15}$ alcohols sold under the trade name "Finsolv TN" or "Witconol TN" by Witco, 2-ethylphenyl benzoate such as the commercial product sold under the name X-Tend 226® by ISP, octyl palmitate, isopropyl lanolate, triglycerides, including those of capric/caprylic acids, dicaprylyl carbonate sold under the name "Cetiol CC" by Cognis, oxyethylenated or oxypropylenated fatty esters and ethers; silicone oils (cyclomethicone, polydimethyl-siloxanes or PDMSs) or fluoro oils, and polyalkylenes.

As waxy compounds, mention may be made of carnauba wax, beeswax, hydrogenated castor oil, polyethylene waxes and polymethylene waxes such as that sold under the name Cirebelle 303 by Sasol.

Among the organic solvents, mention may be made of lower polyols and alcohols. The lower polyols may be chosen from glycols and glycol ethers such as ethylene glycol, propylene glycol, butylene glycol, dipropylene glycol and diethylene glycol.

As hydrophilic thickeners, mention may be made of carboxyvinyl polymers such as carbopols (carbomers) and pemulens (acrylate/$C_{10}$-$C_{30}$ alkyl acrylate copolymers); polyacrylamides such as for example the crosslinked copolymers sold under the names Sepigel 305 (CTFA name: polyacrylamide/$C_{13-14}$ isoparaffin/Laureth 7) or Simulgel 600 (CTFA name: acrylamide/sodium acryloyl-dimethyltaurate copolymer/isohexadecane/polysorbate 80) by Seppic; polymers and copolymers of 2-acrylamido-2-methylpropanesulphonic acid optionally crosslinked and/or neutralized, such as poly(2-acrylamido-2-methylpropanesulphonic acid) sold by Hoechst under the trade name "Hostacerin AMPS" (CTFA name: ammonium polyacryloyldimethyl taurate) or "Simulgel 800" sold by Seppic (CTFA name: sodium polyacryloyldimethyl taurate/polysorbate 80/sorbitan oleate); copolymers of 2-acrylamido-2-methylpropanesulphonic acid and hydroxyethyl acrylate such as Simulgel NS and Sepinov EMT 10 sold by Seppic; cellulose derivatives such as hydroxyethyl cellulose; polysaccharides and especially gums such as xanthan gum; and mixtures thereof.

As lipophilic thickeners, mention may be made of synthetic polymers such as poly($C_{10}$-$C_{30}$ alkyl acrylates) sold under the name "Intelimer IPA 13-1" and "Intelimer IPA 13-6" by Landec or else modified clays such as hectorite and its derivatives, such as the products sold under the name "Bentone".

Among the active ingredients mention may be made of:
vitamins (C, K, PP, etc.) and their derivatives or precursors, alone or as mixtures;
agents for combating pollution and/or free-radical scavengers;
depigmenting agents and/or propigmenting agents;
anti-glycation agents;
soothing agents;
NO-synthase inhibitors;
agents that stimulate the synthesis of dermal or epidermal macromolecules and/or that prevent their degradation;
agents that stimulate fibroblast proliferation;
agents that stimulate keratinocyte proliferation;
myorelaxants;
tensioning agents;
mattifying agents;
keratolytic agents;
desquamating agents;
moisturizers;
anti-inflammatory agents;
agents that act on the energy metabolism of cells;
insect repellents;
substance P antagonists or CRGP antagonists;
agents for preventing hair loss and/or for hair regrowth; and
anti-wrinkle agents.

Of course, a person skilled in the art will be sure to choose the optional additional compound or compounds mentioned above and/or their amounts so that the advantageous properties intrinsically linked to the compositions according to the invention are not, or are not substantially, impaired by the envisaged addition or additions.

The compositions according to the invention may be prepared according to the techniques well known to a person skilled in the art. They may be in particular in the form of a simple or complex (O/W, W/O, O/W/O or W/O/W) emulsion such as a cream, a milk or a cream-gel; in the form of an aqueous gel; or in the form of a lotion. They may also be packaged in an aerosol and be in the form of a foam or spray.

Preferably, the compositions according to the invention are in the form of an oil-in-water or water-in-oil emulsion.

The emulsions generally contain at least one emulsifier chosen from amphoteric, anionic, cationic or non-ionic emulsifiers, used alone or as a mixture. The emulsifiers are chosen in an appropriate manner according to the emulsion to be obtained (W/O or O/W). The emulsions may also contain other types of stabilizers such as for example fillers, gelling polymers or thickeners.

As emulsifying surfactants that can be used for preparing W/O emulsions, mention may be made, for example, of alkyl esters or ethers of sorbitan, of glycerol or of sugars; silicone surfactants, for example dimethicone copolyols, such as the mixture of cyclomethicone and of dimethicone copolyol sold under the name "DC 5225 C" by Dow Corning, and alkyldimethicone copolyols such as laurylmethicone copolyol sold under the name "Dow Corning 5200 Formulation Aid" by Dow Corning; cetyl dimethicone copolyol such as the product sold under the name "Abil EM 90R" by Goldschmidt and the mixture of cetyl dimethicone copolyol, polyglycerol isostearate (4 mol) and hexyl laurate sold under the name "Abil WE 09" by Goldschmidt. It is possible to also add thereto one or more co-emulsifiers, which advantageously may be chosen from the group comprising alkylated polyol esters.

As alkylated polyol esters, mention may be made especially of polyethylene glycol esters, for example PEG-30 dipolyhydroxystearate such as the product sold under the name Arlacel P135 by ICI.

As glycerol and/or sorbitan esters, mention may be made for example of polyglycerol isostearate, such as the product sold under the name Isolan GI 34 by Goldschmidt; sorbitan isostearate, such as the product sold under the name Arlacel 987 by ICI; sorbitan isostearate and glycerol such as the product sold under the name Arlacel 986 by ICI, and mixtures thereof.

For the O/W emulsions, mention may be made, for example as emulsifiers, of non-ionic emulsifiers such as oxyalkylenated (more particularly polyoxyethylenated) fatty acid and glycerol esters; oxyalkylenated fatty acid and sorbitan esters; oxyalkylenated (oxyethylenated and/or oxypropylenated) fatty acid esters such as the PEG-100 stearate/glyceryl stearate mixture sold, for example, by ICI under the name Arlacel 165; oxyalkylenated (oxyethylenated and/or oxypropylenated) fatty alcohol ethers; sugar esters such as sucrose stearate; fatty alcohol and sugar ethers, especially alkylpolyglucosides (APGs) such as decyl glucoside and lauryl glucoside sold, for example, by Henkel under the respective names Plantaren 2000 and Plantaren 1200, cetostearyl glucoside, optionally as a mixture with cetostearyl alcohol, sold for example under the name Montanov 68 by Seppic, under the name Tegocare CG90 by Goldschmidt and under the name Emulgade KE3302 by Henkel, and also arachidyl glucoside, for example in the form of the mixture of arachidyl and behenyl alcohols and arachidyl glucoside sold under the name Montanov 202 by Seppic. According to one particular embodiment of the invention, the mixture of alkyl polyglucoside as defined above with the corresponding fatty alcohol may be in the form of a self-emulsifying composition, as described, for example, in document WO-A-92/06778.

Among the other emulsion stabilizers, use will more particularly be made of the polymers of isophthalic acid or sulphoisophthalic acid, and in particular phthalate/sulphoisophthalate/glycol copolymers, for example, the diethylene glycol/phthalate/isophthalate/1,4-cyclohexanedimethanol copolymer (INCI name: Polyester-5) sold under the names "Eastman AQ polymer" (AQ35S, AQ38S, AQ55S, AQ48 Ultra) by Eastman Chemical.

When an emulsion is involved, the aqueous phase of the latter may comprise a non-ionic vesicular dispersion prepared according to known processes (Bangham, Standish and Watkins, J. Mol. Biol. 13, 238 (1965), FR 2 315 991 and FR 2 416 008).

The compositions according to the invention find their application in a large number of treatments, in particular cosmetic treatments, for the skin, lips and hair, including the scalp, in particular for protecting and/or caring for the skin, lips and/or hair, and/or for making up the skin and/or the lips.

Another subject of the present invention consists of the use of the compositions according to the invention as defined above, for the manufacture of products for the cosmetic treatment of the skin, lips, nails, hair, eyelashes, eyebrows and/or scalp, in particular care products, sunscreen products and makeup products.

The cosmetic compositions according to the invention may, for example, be used as a makeup product.

The cosmetic compositions according to the invention may, for example, be used as a care product and/or sunscreen product for the face and/or the body, of liquid to semi-liquid consistency, such as milks, more or less rich creams, cream-gels or pastes. They may optionally be packaged in an aerosol and may be in the form of a foam or spray.

The compositions according to the invention in the form of vaporizable fluid lotions in accordance with the invention are applied to the skin or the hair in the form of fine particles using pressurized devices. The devices in accordance with the invention are well known to those skilled in the art and comprise non-aerosol pump-dispensers or "atomizers", aerosol containers comprising a propellant and also aerosol pump-dispensers that use compressed air as a propellant. The latter are described in U.S. Pat. No. 4,077,441 and U.S. Pat. No. 4,850,517.

The compositions packaged as an aerosol in accordance with the invention generally contain conventional propellants such as, for example, hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

Concrete, but in no way limiting, examples that illustrate the invention will now be given.

COMPARATIVE SOLUBILITIES OF LIPOPHILIC ACTIVE AGENTS BETWEEN PRIOR-ART SOLVENTS AND THE SOLVENTS OF THE INVENTION

Active Agents Tested

Active Agent 1

Ethyl 4-hydroxyphenylcarbamate

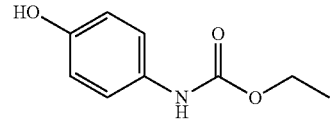

Active Agent 2

2-Hydroxy-5-octanoylbenzoic acid

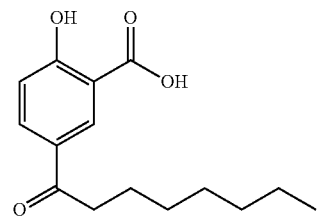 [SMILES: CCCCCCCC(=O)c1ccc(O)c(C(=O)O)c1]

Screening Agents Tested

Screen 1

Octyl (2Z,4E)-5-(diethylamino)-2-(phenyl-sulphonyl)penta-2,4-dienoate (known under the name CKK-92 from FujiFilm)

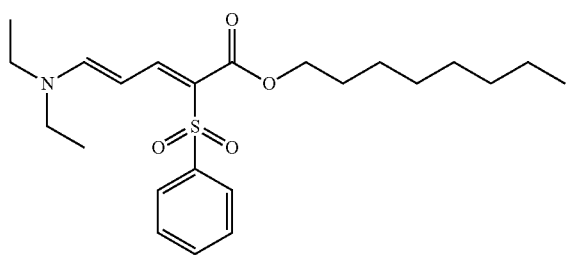 [SMILES: CCCCCCCCOC(=O)/C(=C/C=C/N(CC)CC)S(=O)(=O)c1ccccc1]

Screen 2

(2E)-1-(4-hydroxyphenyl)-3-phenylprop-2-en-1

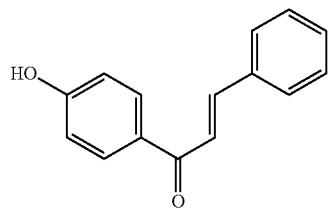 [SMILES: O=C(/C=C/c1ccccc1)c1ccc(O)cc1]

Comparative Oil 1

Eldew SL-205 from Ajinomoto: Isopropyl N-lauroyl sarcosinate of formula

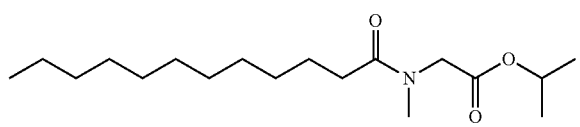 [SMILES: CCCCCCCCCCCC(=O)N(C)CC(=O)OC(C)C]

Comparative Oil 2

Finsolv TN: $C_{12}$-$C_{15}$ alkylbenzoate

Comparative Oil 3

Miglyol 812: Caprylic/capric acid triglycerides

Procedure:

X mg of product are introduced into Y mg of oil; with gentle heating (<60° C.) and the use of a sonicator for 1 minute, the solution obtained is left at laboratory temperature for 1 month; the condition of this solution is observed; if no crystal or oily deposit is visible, the solubility of the product is taken to be greater than X×100/(X+Y) by weight/weight; when crystals or an oily deposit are apparent, the test is repeated with 5% less product.

TABLE 1

| Solvent | Active agent 1 |
|---|---|
| Eldew SL-205 | 23% |
| Miglyol 812 | 3% |
| Finsolv TN | 4% |
| Compound (b) of the invention | 40% |

TABLE 2

| Solvent | Active agent 2 |
|---|---|
| Eldew SL-205 | 18% |
| Miglyol 812 | 4.5% |
| Finsolv TN | 5% |
| Compound (b) of the invention | 48% |
| Compound (c) of the invention | 29% |

TABLE 3

| Solvent | Screen 1 |
|---|---|
| Eldew SL-205 | 35% |
| Miglyol 812 | 16% |
| Finsolv TN | 30% |
| Compound (b) of the invention | 62% |
| Compound (c) of the invention | 40% |

TABLE 4

| Solvent | Screen 2 |
|---|---|
| Eldew SL-205 | 15% |
| Miglyol 812 | 2% |
| Finsolv TN | 3% |
| Compound (b) of the invention | 25% |

The following formulations were prepared, the amounts being expressed as percentages by weight in relation to the total weight of the composition.

| Composition | Ex. 1 | Ex. 2 | Ex. 3 | Ex. 4 |
|---|---|---|---|---|
| | Phase A | | | |
| Polydimethylsiloxane | 0.5 | 0.5 | 0.5 | 0.5 |
| Preservatives | 1 | 1 | 1 | 1 |
| Stearic acid | 1.5 | 1.5 | 1.5 | 1.5 |
| Glyceryl monostearate/PEG100 stearate mixture | 1 | 1 | 1 | 1 |
| Mixture of cetylstearyl glucoside and cetyl and stearyl alcohols | 2 | 2 | 2 | 2 |
| Cetyl alcohol | 0.5 | 0.5 | 0.5 | 0.5 |
| Compound (b) | 20 | | 15 | — |
| Compound (c) | | 20 | | 15 |
| Bis{ethylhexyloxy-2-hydroxyphenyl}-6-(methoxyphenyl)-1,3,5-triazine (TINOSORB S-CIBA) | 5 | 5 | | |
| 2,4,6-Tris[(ethylhexyloxy- | — | — | 5 | 5 |

| Composition | Ex. 1 | Ex. 2 | Ex. 3 | Ex. 4 |
|---|---|---|---|---|
| carbonyl)anilino]-1,3,5-triazine (Uvinul T150-BASF) | | | | |
| Phase B | | | | |
| Deionized water | qs 100 | qs 100 | qs 100 | qs 100 |
| Glycerol | 5 | 5 | 5 | 5 |
| Xanthan gum | 0.2 | 0.2 | 0.2 | 0.2 |
| Monocetyl phosphate | 1 | 1 | 1 | 1 |
| Phase C | | | | |
| Isohexadecane | 1 | 1 | 1 | 1 |
| Acrylic acid/stearyl methacrylate copolymer | 0.2 | 0.2 | 0.2 | 0.2 |
| Triethanolamine | qs pH | qs pH | qs pH | qs pH |

Procedure:

The aqueous phase (phase B) containing all of its ingredients is heated at 80° C. on a water bath. The fatty phase (phase A) containing all of its ingredients is heated at 80° C. on a water bath. A is emulsified in B with stirring using a rotor-stator (apparatus from Moritz). Phase C is incorporated and the mixture is allowed to return to ambient temperature with moderate stirring. Triethanolamine is introduced so as to adjust the pH to the value desired at the end of manufacture. The antisun emulsions obtained are stable on storage and do not exhibit any crystals or precipitates.

The invention claimed is:

1. A method of dissolving an active agent in a liquid fatty phase and/or improving the solubility of the active agent in the fatty phase, which comprises including at least one piperidine ester derivative of formula (I) below:

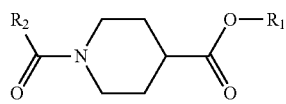

in which:
$R_1$ is a linear or branched $C_1$-$C_{12}$ alkyl radical,
$R_2$ is a linear or branched $C_1$-$C_{20}$ alkyl radical,
with the proviso that the sum of the carbon atoms for $R_1$ and $R_2$ is from 2 to 22,
in a composition comprising, in a cosmetically acceptable medium, at least one liquid fatty phase and at least one lipophilic active agent, and containing no dibenzoylmethane-type UV screening agent.

2. The method according to claim 1, wherein the compound of formula (I) is selected from compounds (a) to (c) below:

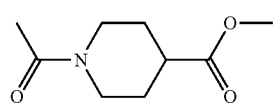

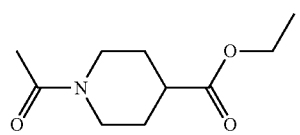

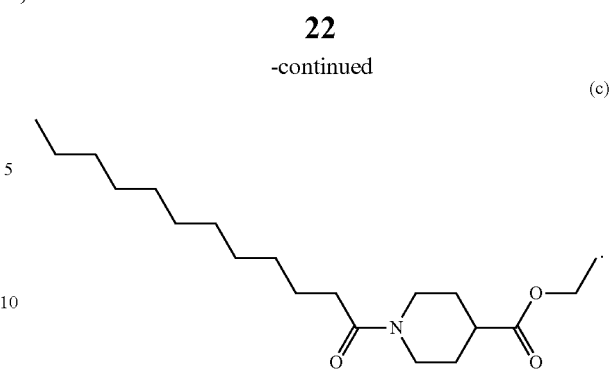

3. The method according to claim 1, wherein the at least one piperidine ester derivative of formula (I) constitutes the sole solvent of the lipophilic active agent(s).

4. The method according to claim 1, wherein the lipophilic active agent is selected from lipophilic organic UV screening agents.

5. The method according to claim 4, wherein the lipophilic screening agent is selected from the group consisting of para-aminobenzoic acid derivatives, salicylic derivatives, cinnamic derivatives, benzophenones and aminobenzophenones, anthranillic derivatives, β,β-diphenylacrylate derivatives, benzylidenecamphor derivatives, phenylbenzimidazole derivatives, benzotriazole derivatives, triazine derivatives, bisresorcinyl triazines, imidazoline derivatives, benzalmalonate derivatives, 4,4-diarylbutadiene derivatives, benzoxazole derivatives, merocyanines, malonitrile and malonate diphenyl butadiene derivatives, chalcones and mixtures thereof.

6. The method according to claim 5, wherein the lipophilic organic UV screening agent is selected from the group consisting of triazines, merocyanines, benzotriazoles, chalcones, benzophenones aminobenzophenones and derivatives from the group consisting of the malonitrile and malonate diphenyl butadienes.

7. The method according to claim 1, wherein the lipophilic active agent is selected from the group consisting of aminophenol derivatives, salicylic acid derivatives, N,N'-di(arylmethylene)ethylenediaminetriacetate derivatives, 2-amino-4-alkylaminopyrimidine 3-oxide derivatives, flavonoids, retinol and derivatives thereof, carotenoids, fragrances, essential oils, hormones, vitamins, ceramides and mixtures thereof.

8. A composition comprising, in a cosmetically acceptable medium, at least one liquid fatty phase, wherein the composition comprises at least one piperidine ester derivative of formula (I) below:

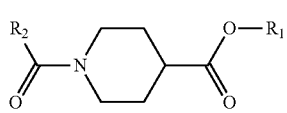

in which:
$R_1$ is a linear or branched $C_1$-$C_{12}$ alkyl radical,
$R_2$ is a linear or branched $C_1$-$C_{20}$ alkyl radical,
with the proviso that the sum of the carbon atoms for $R_1$ and $R_2$ is from 2 to 22,
and at least one liquid fatty phase and at least one lipophilic active agent, and the compositions does not contain a dibenzoylmethane-type UV screening agent.

9. The composition according to claim 8, wherein the lipophilic active agent is selected from lipophilic organic UV screening agents.

10. The composition according to claim 9, wherein the lipophilic screening agent is selected from the group consisting of para-aminobenzoic acid derivatives, salicylic derivatives, cinnamic derivatives, benzophenones and aminobenzophenones, anthranillic derivatives, β,β-diphenylacrylate derivatives, benzylidenecamphor derivatives, phenylbenzimidazole derivatives, benzotriazole derivatives, triazine derivatives, bisresorcinyl triazines, imidazoline derivatives, benzalmalonate derivatives, 4,4-diarylbutadiene derivatives, benzoxazole derivatives, merocyanines, malonitrile and malonate diphenyl butadiene derivatives, chalcones and mixtures thereof.

11. The composition according to claim 10, wherein the lipophilic organic UV screening agent is selected from the group consisting of triazines, merocyanines, benzotriazoles, chalcones, benzophenones and aminobenzophenones and derivatives from the group consisting of the malonitrile and malonate diphenyl butadienes.

12. The composition according to claim 8, wherein the lipophilic active agent is selected from the group consisting of aminophenol derivatives, salicylic acid derivatives, N,N'-di(arylmethylene)ethylenediaminetriacetate derivatives, 2-amino-4-alkylaminopyrimidine 3-oxide derivatives, flavonoids, retinol and derivatives thereof, carotenoids, fragrances, essential oils, hormones, vitamins, ceramides and mixtures thereof.

13. The composition according to claim 8, wherein the at least one piperidine ester derivative of formula (I) is present in the composition at contents of from 1% to 30% by weight, relative to the total weight of the composition.

14. The method according to claim 1 comprising improving the effectiveness of said active agent and/or the cosmetic qualities and/or the stability of said composition.

15. The method according to claim 1 comprising improving the sun protection factor.

16. The method according to claim 2, wherein the at least one piperidine ester derivative of formula (I) constitutes the sole solvent of the lipophilic active agent(s).

17. The method according to claim 2, wherein the lipophilic active agent is selected from lipophilic organic UV screening agents.

18. The method according to claim 3, wherein the lipophilic active agent is selected from lipophilic organic UV screening agents.

19. The method according to claim 2, wherein the lipophilic active agent is selected from the group consisting of aminophenol derivatives, salicylic acid derivatives, N,N'-di(arylmethylene)ethylenediaminetriacetate derivatives, 2-amino-4-alkylaminopyrimidine 3-oxide derivatives, flavonoids, retinol and derivatives thereof, carotenoids, fragrances, essential oils, hormones, vitamins, ceramides and mixtures thereof.

20. The method according claim 3, wherein the lipophilic active agent is selected from the group consisting of aminophenol derivatives, salicylic acid derivatives, N,N'-di(arylmethylene)ethylenediaminetriacetate derivatives, 2-amino-4-alkylaminopyrimidine 3-oxide derivatives, flavonoids, retinol and derivatives thereof, carotenoids, fragrances, essential oils, hormones, vitamins, ceramides and mixtures thereof.

21. The composition according to claim 8, wherein the compound of formula (I) is selected from compounds (a) to (c) below:

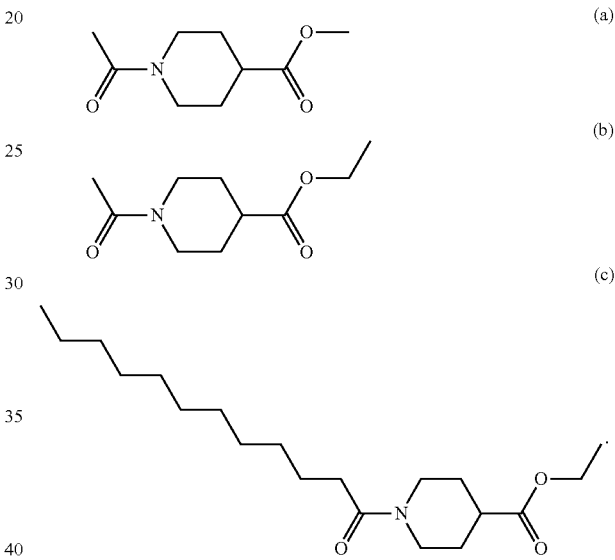

22. The composition according to claim 8, wherein the at least one piperidine ester derivative of formula (I) is present in the composition at contents from 3% to 20% by weight, relative to the total weight of the composition.

23. The composition according to claim 8, wherein the at least one piperidine ester derivative of formula (I) constitutes the sole solvent of the lipophilic active agent(s).

* * * * *